(12) United States Patent
Vivenzio et al.

(10) Patent No.: US 8,652,057 B2
(45) Date of Patent: Feb. 18, 2014

(54) RECYCLABLE OR BIODEGRADABLE BLOOD PRESSURE CUFF

(75) Inventors: Robert L. Vivenzio, Auburn, NY (US); Ian K. Edwards, Skaneateles, NY (US); Raymond A. Lia, Auburn, NY (US); Jeffrey Perkins, Tully, NY (US); Sean R. Karla, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 532 days.

(21) Appl. No.: 12/704,638

(22) Filed: Feb. 12, 2010

(65) Prior Publication Data

US 2010/0298725 A1 Nov. 25, 2010

Related U.S. Application Data

(63) Continuation-in-part of application No. 12/468,438, filed on May 19, 2009.

(51) Int. Cl.
*A61B 5/02* (2006.01)

(52) U.S. Cl.
USPC .......................... 600/499; 600/490

(58) Field of Classification Search
USPC .................. 600/481, 485, 490–499
See application file for complete search history.

(56) References Cited

U.S. PATENT DOCUMENTS

| 1,106,341 | A | 8/1914 | Bristol |
|---|---|---|---|
| 1,328,876 | A | 1/1920 | Hill |
| 1,377,032 | A | 5/1921 | Starling et al. |
| 1,729,297 | A | 9/1929 | Stewart |
| 2,087,494 | A | 7/1937 | Annin |
| 2,341,137 | A | 2/1944 | Damron |
| 2,564,669 | A | 8/1951 | Brady |
| 2,636,394 | A | 4/1953 | Melchior |
| 2,678,040 | A | 5/1954 | Poole et al. |
| 2,714,379 | A | 8/1955 | Raines |
| 3,279,459 | A | 10/1966 | Schenker |
| 3,473,525 | A | 10/1969 | Hanafin |
| 3,606,880 | A | 9/1971 | Ogle, Jr. |
| 3,633,567 | A | 1/1972 | Sarnoff |
| 3,635,214 | A | 1/1972 | Rand et al. |
| 3,659,592 | A | 5/1972 | Natkanski |

(Continued)

FOREIGN PATENT DOCUMENTS

| CA | 2100854 | 1/1994 |
|---|---|---|
| DE | 0591564 | 1/1934 |

(Continued)

OTHER PUBLICATIONS

International Search Report and Written Opinion for PCT/US2011/053376, Dated May 4, 2012 (9 pages).

(Continued)

*Primary Examiner* — Patricia Mallari
*Assistant Examiner* — Tiffany Weston

(57) ABSTRACT

A blood pressure cuff is defined by a first sheet, having an opening, and a second sheet. The second sheet is attached to a bottom of the first sheet to form an interior inflatable portion between the first sheet and the second sheet, with the opening of the first sheet fluidly interconnecting the interior inflatable portion with an exterior of the cuff. The blood pressure cuff is made from a single type of material and can be recycled, biodegradable, or composted.

27 Claims, 12 Drawing Sheets

(56) References Cited

U.S. PATENT DOCUMENTS

| | | | |
|---|---|---|---|
| 3,756,239 A | 9/1973 | Smythe | |
| 3,757,772 A | 9/1973 | Goldblat et al. | |
| 3,760,795 A | 9/1973 | Adelhed | |
| 3,773,036 A * | 11/1973 | Weyer | 600/499 |
| 3,797,315 A | 3/1974 | Halpern | |
| 3,805,618 A | 4/1974 | Csaposs et al. | |
| 3,874,242 A | 4/1975 | Csaposs et al. | |
| 3,906,937 A | 9/1975 | Aronson | |
| 3,977,393 A * | 8/1976 | Kovacic | 600/499 |
| D244,879 S | 6/1977 | Manno | |
| 4,036,061 A | 7/1977 | Speidel | |
| 4,036,216 A | 7/1977 | Ramsey, III | |
| 4,040,298 A | 8/1977 | Lee et al. | |
| 4,248,241 A | 2/1981 | Tacchi | |
| 4,255,970 A | 3/1981 | Van Pottelberg | |
| D269,905 S | 7/1983 | Tamm | |
| 4,501,271 A | 2/1985 | Clifton et al. | |
| 4,535,938 A | 8/1985 | Lindabury, Sr. | |
| 4,543,824 A | 10/1985 | Marterer | |
| 4,548,249 A | 10/1985 | Slaughterbeck | |
| 4,549,550 A | 10/1985 | Kami | |
| 4,605,010 A | 8/1986 | McEwen | |
| 4,653,506 A | 3/1987 | Romanovskaya | |
| 4,685,336 A | 8/1987 | Lee | |
| 4,726,382 A | 2/1988 | Boehmer et al. | |
| 4,726,686 A | 2/1988 | Wolf et al. | |
| 4,802,370 A | 2/1989 | EerNisse et al. | |
| 4,844,512 A | 7/1989 | Gahwiler | |
| 4,896,676 A | 1/1990 | Sasaki | |
| 4,920,971 A | 5/1990 | Blessinger | |
| 4,967,758 A | 11/1990 | Masciarotte | |
| 4,979,953 A | 12/1990 | Spence | |
| 5,003,981 A | 4/1991 | Kankkunen et al. | |
| 5,025,792 A | 6/1991 | Hon et al. | |
| 5,048,533 A | 9/1991 | Muz | |
| 5,101,830 A | 4/1992 | Duffy et al. | |
| 5,137,024 A | 8/1992 | Souma | |
| 5,179,957 A | 1/1993 | Williams | |
| 5,181,422 A | 1/1993 | Leonard et al. | |
| 5,220,925 A | 6/1993 | Hishida | |
| 5,228,448 A | 7/1993 | Byrd | |
| 5,251,646 A | 10/1993 | Bowen | |
| 5,275,444 A | 1/1994 | Wythoff | |
| 5,320,169 A | 6/1994 | Delatore | |
| 5,392,782 A | 2/1995 | Garrett | |
| D356,155 S | 3/1995 | Caven | |
| 5,396,894 A * | 3/1995 | Eide et al. | 600/499 |
| 5,400,787 A | 3/1995 | Marandos | |
| 5,413,582 A | 5/1995 | Eaton | |
| 5,424,598 A | 6/1995 | Corbett | |
| 5,511,552 A | 4/1996 | Johnson | |
| 5,513,534 A | 5/1996 | Brechbuhl et al. | |
| 5,513,643 A | 5/1996 | Suite | |
| 5,626,142 A | 5/1997 | Marks | |
| 5,660,182 A | 8/1997 | Kuroshaki et al. | |
| 5,678,558 A | 10/1997 | Johnson | |
| 5,690,672 A | 11/1997 | Cohen | |
| 5,746,213 A | 5/1998 | Marks | |
| 5,753,821 A | 5/1998 | Chou | |
| 5,797,851 A | 8/1998 | Byrd | |
| 5,819,739 A | 10/1998 | Levavi et al. | |
| 5,882,515 A | 3/1999 | Lacy et al. | |
| 5,904,655 A | 5/1999 | Brackett | |
| 5,966,829 A | 10/1999 | Lia et al. | |
| 6,036,718 A | 3/2000 | Ledford et al. | |
| 6,082,170 A | 7/2000 | Lia et al. | |
| 6,095,983 A | 8/2000 | Wawro | |
| 6,120,458 A | 9/2000 | Lia et al. | |
| 6,149,600 A | 11/2000 | Poorman-Ketchum | |
| 6,152,880 A | 11/2000 | Okada | |
| 6,168,566 B1 | 1/2001 | Lia et al. | |
| 6,189,558 B1 | 2/2001 | Traylor | |
| 6,213,953 B1 | 4/2001 | Reeves | |
| 6,234,972 B1 | 5/2001 | Lia et al. | |
| 6,245,023 B1 | 6/2001 | Clemmons | |
| 6,245,024 B1 | 6/2001 | Montagnino et al. | |
| 6,344,025 B1 | 2/2002 | Inagaki et al. | |
| 6,346,084 B1 | 2/2002 | Schnell et al. | |
| 6,364,843 B1 | 4/2002 | Lightle | |
| 6,394,977 B1 | 5/2002 | Taylor et al. | |
| 6,422,086 B1 | 7/2002 | Dromms et al. | |
| 6,475,153 B1 | 11/2002 | Khair et al. | |
| 6,481,291 B1 | 11/2002 | Lia et al. | |
| 6,506,162 B1 | 1/2003 | Tseng | |
| 6,525,238 B2 * | 2/2003 | Corrales | 600/499 |
| 6,551,249 B2 | 4/2003 | Ashida et al. | |
| 6,578,428 B1 | 6/2003 | Dromms et al. | |
| 6,615,666 B1 | 9/2003 | Lia et al. | |
| 6,616,666 B1 | 9/2003 | Michelson | |
| 6,682,547 B2 | 1/2004 | McEwen et al. | |
| 6,746,406 B2 | 6/2004 | Lia et al. | |
| 6,796,186 B2 | 9/2004 | Lia et al. | |
| D532,519 S | 11/2006 | Aujla et al. | |
| D568,478 S | 5/2008 | Karla et al. | |
| 7,722,542 B2 | 5/2010 | Lia et al. | |
| 7,780,698 B2 | 8/2010 | McEwen et al. | |
| 8,147,417 B2 * | 4/2012 | Gavriely | 600/499 |
| 2001/0005777 A1 * | 6/2001 | Nakagawa et al. | 600/499 |
| 2002/0099297 A1 | 7/2002 | Nakagawa et al. | |
| 2002/0156382 A1 | 10/2002 | Freund et al. | |
| 2003/0036690 A1 | 2/2003 | Geddes et al. | |
| 2003/0135123 A1 | 7/2003 | Dromms et al. | |
| 2004/0049114 A1 | 3/2004 | Alesse | |
| 2004/0083816 A1 | 5/2004 | Lia et al. | |
| 2004/0092831 A1 | 5/2004 | Hood, Jr. | |
| 2004/0181156 A1 | 9/2004 | Kingsford et al. | |
| 2005/0171445 A1 | 8/2005 | Millay et al. | |
| 2006/0089668 A1 | 4/2006 | Warburton | |
| 2006/0217618 A1 | 9/2006 | Lia et al. | |
| 2006/0293600 A1 | 12/2006 | Wawro et al. | |
| 2007/0135836 A1 | 6/2007 | McEwen et al. | |
| 2007/0244506 A1 | 10/2007 | McEwen et al. | |
| 2008/0114320 A1 | 5/2008 | Beck et al. | |
| 2008/0243010 A1 | 10/2008 | Kulik | |
| 2009/0171223 A1 * | 7/2009 | McEwen et al. | 600/490 |
| 2010/0089408 A1 | 4/2010 | McCaughey et al. | |
| 2010/0186752 A1 | 7/2010 | Rixon | |

FOREIGN PATENT DOCUMENTS

| | | | |
|---|---|---|---|
| DE | 2220233 | 11/1973 | |
| EP | 0591564 | 4/1994 | |
| EP | 0705563 | 4/1996 | |
| EP | 1945096 | 7/2008 | |
| EP | 1992281 | 11/2008 | |
| FR | 2592297 | 7/1987 | |
| GB | 740181 | 11/1955 | |
| JP | 11197124 | 7/1999 | |
| JP | 2002253518 | 9/2002 | |
| WO | WO 00/22983 | 4/2000 | |
| WO | WO 00/40941 | 7/2000 | |
| WO | WO 02/26128 | 4/2002 | |
| WO | WO 2007/035271 | 3/2007 | |
| WO | WO 2007/116588 | 10/2007 | |
| WO | WO 2007116588 | * 10/2007 | A61B 5/022 |
| WO | WO 2007/125546 | 11/2007 | |
| WO | 2011/130020 A1 | 10/2011 | |

OTHER PUBLICATIONS

Welch Allyn DuraShock Integrated Aneroid Sphygmomanometer Operating Instructional Manual (8 pages).

Invitation to Pay Additional Fees and, Where Applicable, Protest Fee for PCT/US10/35062, Dated Jul. 20, 2010 (7 pages).

Invitation to Pay Additional Fees and, Where Applicable, Protest Fee for PCT/US10/35065, Dated Jul. 20, 2010 (7 pages).

International Search Report and Written Opinion for PCT/US010/35062, Dated Sep. 28, 2010 (16 pages).

International Search Report and Written Opinion for PCT/US010/35065, Dated Sep. 27, 2010 (16 pages).

Alpert, et al., "The papercuff, a new disposable blood pressure cuff", Dept. of Pediatrics, University of Tennessee School of Medicine, Manuscript Oct. 3, 1995 (2 pages).

(56) References Cited

OTHER PUBLICATIONS

"Plastics Plus, Inc. Biodegradable Solution PPI BD-0701"; Published Oct. 2008 (8 pages).
"Socket", The American Heritage Dictionary of the English Language .COPYRGT. Houghton Mifflin Company 2003. Retrieved Nov. 7, 2007 from http://www.credoreference.com/entry/4133272.
International Search Report and Written Opinion for PCT/US07/16828, Dated Jan. 18, 2008 (7 pages).
International Search Report for PCT/US06/34909, Dated Feb. 5, 2007 (6 pages).
Supplementary European Search Report for EP 06 79 0195, Dated Oct. 30, 2009 (11 pages).
Welch Allyn DuraShock Integrated Aneroid Sphygmomanometer Operating Instructional Manual (8 pages), 2001.

* cited by examiner

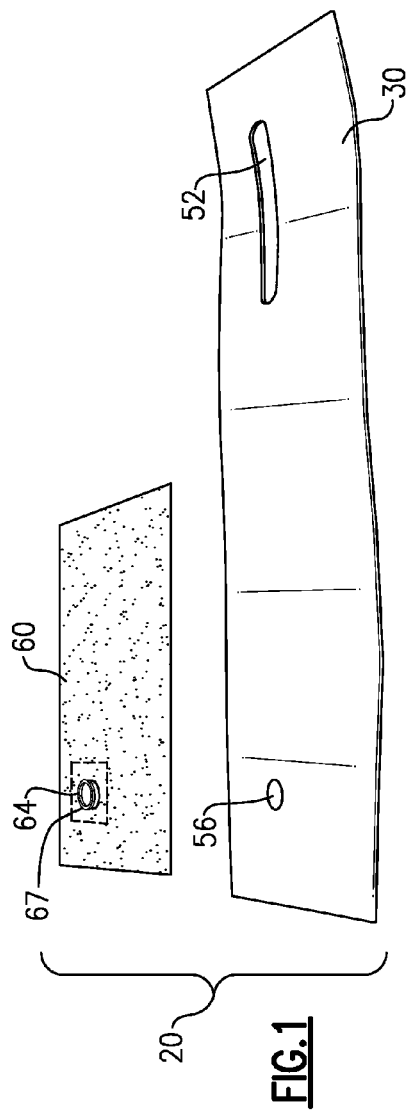
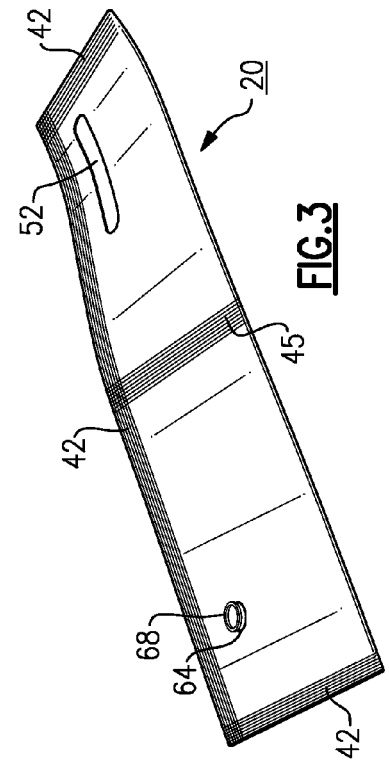
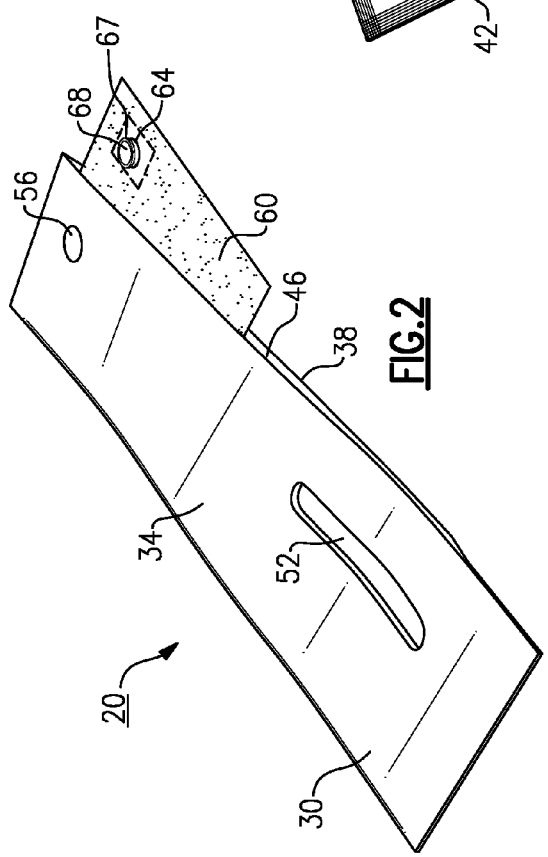

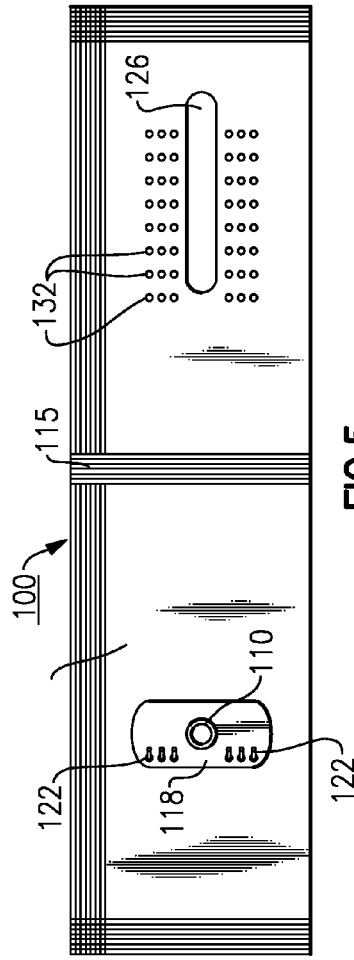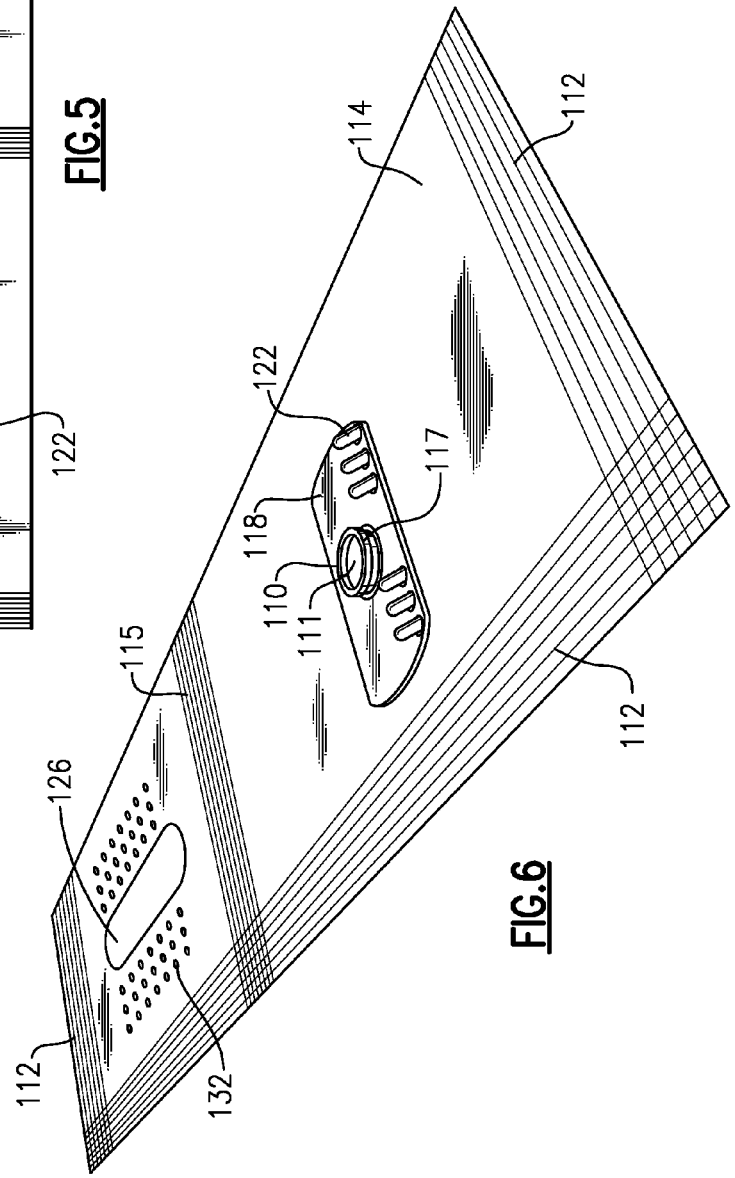

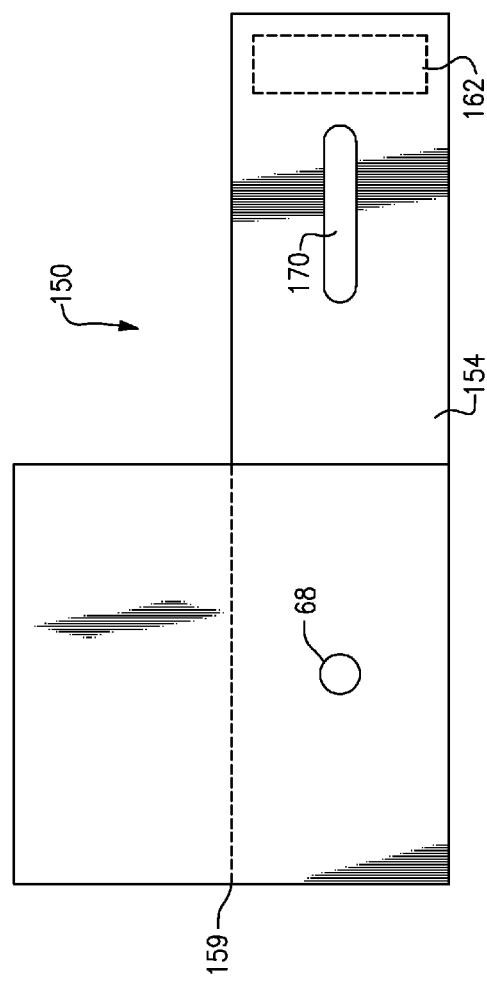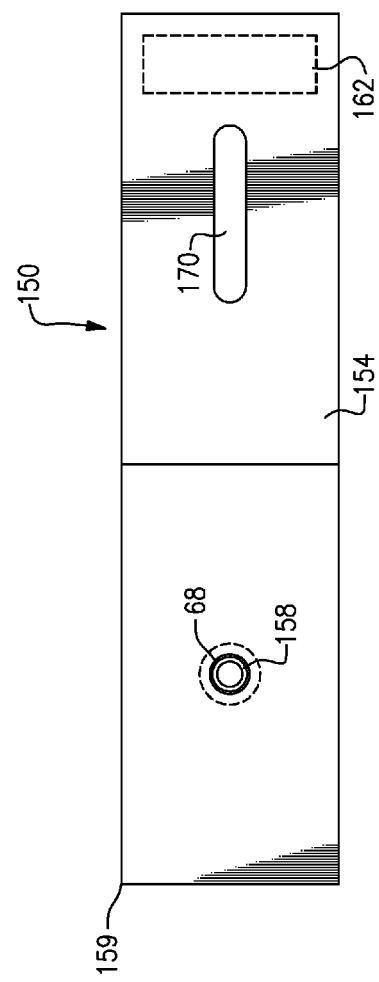

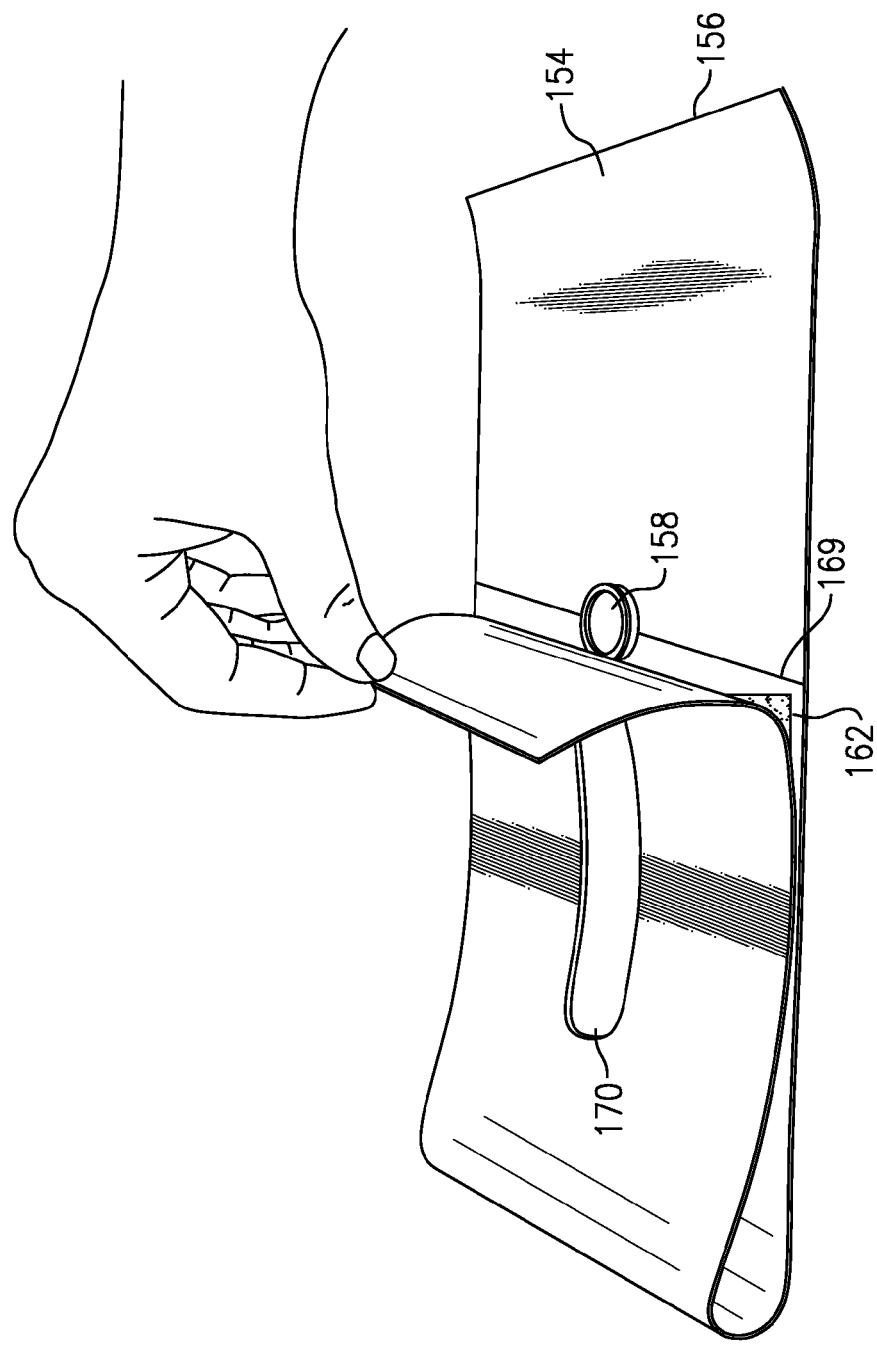

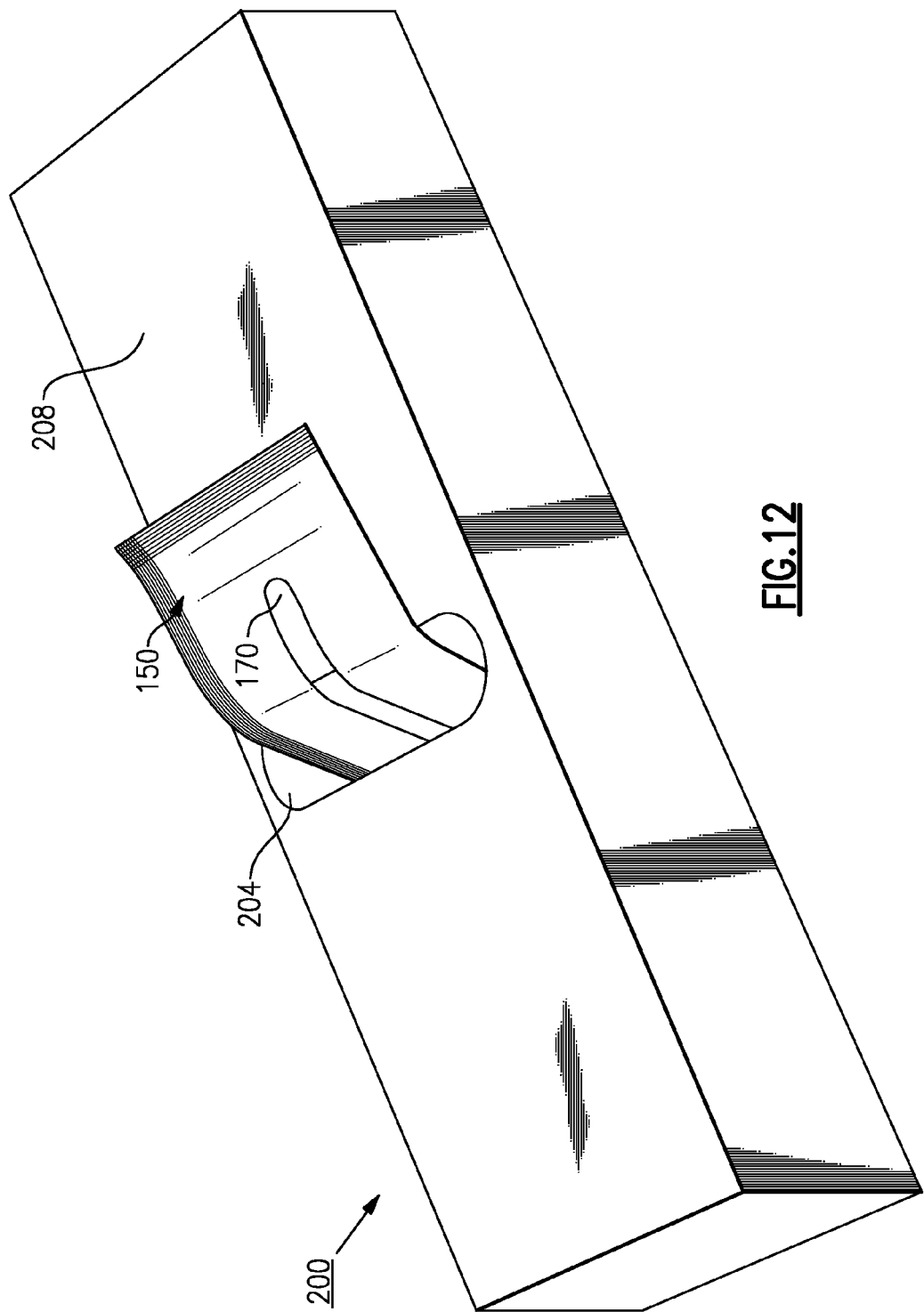

RECYCLABLE OR BIODEGRADABLE BLOOD PRESSURE CUFF

CROSS-REFERENCE TO RELATED APPLICATIONS

This patent application is a continuation-in-part under 37 C.F.R. §1.53(b) and claims benefit of priority to co-pending and commonly owned U.S. non-provisional patent application Ser. No. 12/468,438 filed on May 19, 2009, and entitled "Recyclable or Biodegradable Blood Pressure Cuff"; the contents of which are relied upon and incorporated herein by reference.

FIELD OF THE APPLICATION

This application generally relates to the field of medical diagnostic instruments and more specifically to a low cost, ecologically friendly blood pressure sleeve or cuff that is biodegradable or capable of being recycled.

BACKGROUND OF THE INVENTION

Sphygmomanometers are commonly known and established medical diagnostic instruments used for measuring patient blood pressure. In one well known version, a reusable cuff or sleeve made from fluid-impermeable material is wrapped about the limb (e.g., arm or leg) of the patient. Various sized sleeves are made, depending on the class (i.e., child, adult, neonatal) of the patient. Most sleeves of this type are defined by either a pair of planar sheets that are sealed together or are formed from a single sheet, the sleeve either having a contained bladder or an inflatable interior compartment. These sleeves further typically include hook and loop fasteners disposed at specific locations on opposing sides in order to permit releasable and adjustable attachment to and removal of the sleeve from a patient. The bladder or interior inflatable compartment is inflated using pneumatic means, such as a pump, which is tethered to the cuff by means of a flexible hose attached to a barb that is provided on the exterior of the sleeve. Pressure variations in the sleeve can then be detected by a gage housing having a dial indicator that is attached to the cuff. In mechanical versions, the gage housing contains a movement mechanism having a pressure responsive element, such as a diaphragm, wherein pressure variations are imparted to a dial indicator on the gage housing, according to the well-known oscillometric technique. Electronic blood pressure measuring versions, which may or may not include a pump directly within the gage housing, are also known, such as those manufactured by Welch Allyn, Inc. and Omron Corporation, among others, the results being displayed for example, using an LCD. In the latter types of devices, either the oscillometric (pulsatile) method or the auscultatory method of pressure measurement can be utilized, the latter being used in combination with a stethoscope or microphone.

These diagnostic instruments are repletely found in a doctor's office or within examination rooms within a medical facility or a hospital. With regard to a medical facility or hospital and depending upon the number of procedures that are performed on a patient during an examination or a typical hospital or urgent care visit, there are reasons why a blood pressure sleeve should not be reused, for example, the potential for cross contamination of infectious fluids between patients, among others.

Therefore, there is a need presently to inexpensively provide a disposable blood pressure sleeve, without degrading quality or accuracy in measurement or the use of same.

In the course of developing a sleeve that is disposable, additional consideration must be made with regard to environmental/ecological issues, including landfill, emission and other related concerns.

SUMMARY OF THE INVENTION

According to one aspect, there is disclosed a blood pressure cuff comprising a first sheet having an opening and a second sheet attached to the bottom of the first sheet. An interior-inflatable portion is formed between the first sheet and second sheet such that the opening of the first sheet fluidly interconnects the interior-inflatable portion with the exterior of the cuff. Further, the cuff is made from a single type of material, such as polyethylene, polyester, polyvinylchloride, or polypropylene, to facilitate recycling by having all components classified under a single recycling code. The opening of the cuff is fitted with a socket capable of receiving a gage housing and/or a hose adapter.

The cuff is also configured to be releasably attachable onto the limb of a patient in overlaying relation, with the length of the first sheet and the length of the second sheet being substantially parallel to each other when the cuff is wrapped about the limb. A slot on the first sheet, which is spaced apart from the inflatable portion, advantageously provides a limit to the range of limb circumferences to which the cuff can be attached by limiting the range of movement of the socket as it is engaged with the slot. For example, various child/adult and neonatal cuff versions can be provided.

In one version, the cuff can be secured to the patient for wrapping by, for example, adhesives, clips, hook and loop fasteners or using other releasable means. For example, the first sheet can including a hook attached to an end portion of the bottom of the first sheet, spaced apart from the second sheet, and adjacent the slot. In order to attach to a limb, the top of the first sheet includes a loop fastener, preferably formed from a non-woven fibrous material, to engage the hook and to prevent the cuff from slipping off the limb.

According to yet another aspect, the non-woven fibrous material of the first sheet has a weight of about 0.5 to 3.0 ounces per square yard. Laminated to the bottom of the first sheet is a film, which provides a smooth texture, having a thickness of about 0.002 to 0.008 inches and a weight of about 1.0 to 7.0 ounces per square yard. The creep elongation of the first sheet is less than 0.0065 inches. The top of the second sheet may also include a non-woven fibrous material, but is configured to resist engagement with portions of the first sheet to facilitate attachment of the cuff.

In another aspect, the cuff further includes means for indicating that the cuff has already been used. For example, the color of the cuff may be altered after exposure to light, or the fasteners on the top of the first sheet may be designed to degrade after subsequent removal from hooks on the bottom of the first sheet of the cuff.

In another version of the cuff, the length of the first sheet is sized to allow the cuff to be wrapped around a limb at least two times or is sized to fully overlap the inflatable portion when the cuff is wrapped around a limb of a patient. Such a configuration allows a bottom portion of the first sheet to be fastened to a top portion of the first sheet separate from the inflatable portion of the first sheet.

According to one embodiment, a blood pressure cuff treated with an additive that renders the cuff biodegradable, the cuff including a first sheet having an opening, and a second sheet attached to the bottom of the first sheet. The cuff further includes an inflatable portion between the first sheet and second sheet, where the opening of the first sheet fluidly interconnects the interior inflatable portion with an exterior of the cuff. The material of the cuff can be made from one or more of, for example, polypropylene, polyester, polyvinylchloride, and polyethylene. The first sheet of the cuff has a weight of about 1.5 to 10.0 ounces per square yard and a creep elongation of less than 0.0065 inches.

In yet another embodiment, a method for manufacturing a blood pressure cuff is disclosed. The method for manufacturing a blood pressure cuff includes providing a first sheet with a slotted portion and a bottom surface being made from a fluid impermeable material, and providing a second sheet having a bottom surface also made from a fluid impermeable material. The method further includes attaching a socket to an opening of the first sheet and attaching a portion of the bottom surface of the second sheet to a portion of the bottom of the first sheet including the opening. In this manner, an inflatable portion between the first sheet and second sheet is formed. Further, the opening of the first sheet fluidly interconnects the interior inflatable portion with an exterior of the cuff.

Another aspect includes attaching a fastening means to the bottom surface of the first sheet and being spaced apart from the inflatable portion. Further, the slotted portion is sized to limit the range of limb circumferences to which the cuff can be attached and to permit the attachment of pneumatic means to the opening, which permits inflation and deflation of the cuff. The material of the assembled cuff may include a single type of recyclable material or may be a biodegradable material.

In yet another aspect, the cuff includes providing closure means for releasably securing the cuff in a wrapped configuration. The closure means include, for example, hook and loop fasteners wherein the exterior surface of the cuff is made from a material that provides adhesion to a hook fastener portion of the cuff, thereby serving as loop fasteners.

These and other features and advantages will become readily apparent from the following Detailed Description, which should be read in conjunction with the accompanying drawings.

BRIEF DESCRIPTION OF THE DRAWINGS

FIG. 1 is a partially exploded view of a disposable blood pressure cuff according to a first embodiment;

FIG. 2 is a partially assembled view of the disposable blood pressure cuff of FIG. 1;

FIG. 3 is a top perspective view of the disposable blood pressure cuff of FIGS. 1 and 2;

FIG. 5 is a top plan view of a blood pressure cuff made in accordance with a second embodiment;

FIG. 6 is a top perspective view of the disposable blood pressure cuff of FIG. 5;

FIG. 8d is a perspective view of an unfolded disposable blood pressure cuff made in accordance with yet another embodiment;

FIG. 8e is a perspective view of the disposable blood pressure cuff of FIG. 8d in an assembled state;

FIG. 9 is a perspective view of the disposable blood pressure cuff of FIG. 8, shown in a partially wrapped condition;

FIG. 12 is a top perspective view of a container packaging a plurality of stacked disposable blood pressure cuffs.

DETAILED DESCRIPTION

Figure 4:
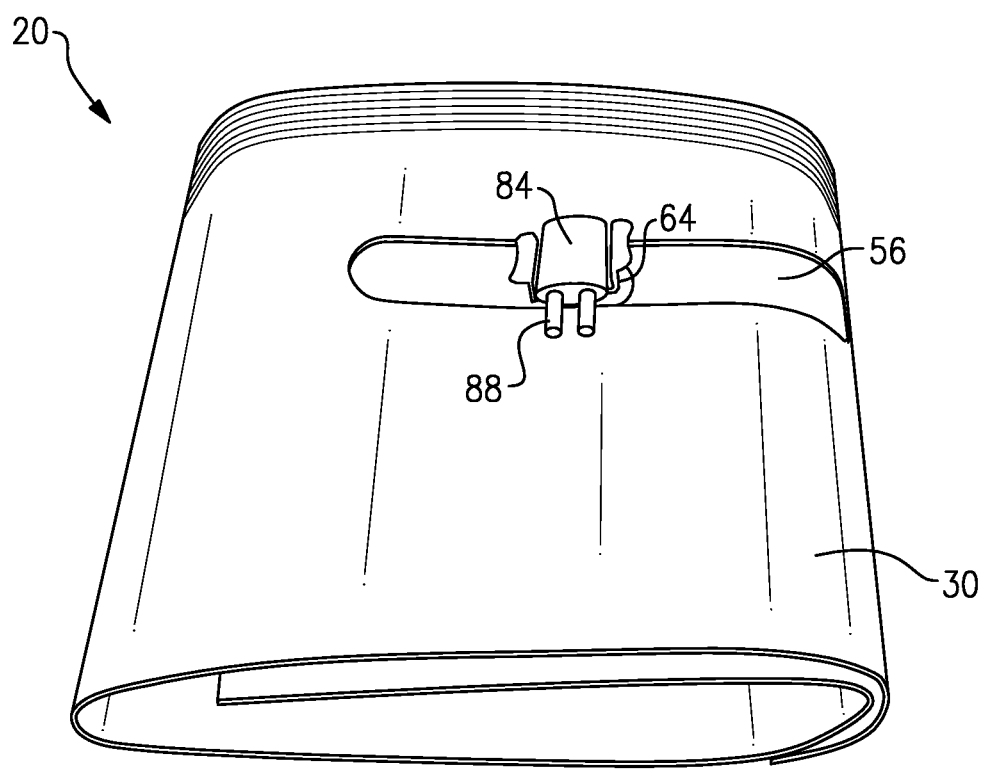
FIG. 4 is a top perspective view of the disposable blood pressure cuff of FIGS. 1-3 shown in a wrapped condition, the cuff having a port connector attached to the port of the cuff.

The following description relates to several exemplary embodiments of a disposable, single use or single patient blood pressure cuff or sleeve, as well as packaging for dispensing the sleeves and related methods for dispensing and packaging the disposable sleeves. It will be readily apparent, however, that a number of other variations and modifications embodying the inventive concepts described herein are possible. In addition, certain terms such as, "top", "bottom", "upper", "lower", "above", "below", "over", "beneath", "left", "right", and the like are used throughout in order to provide a suitable frame of reference with regard to the accompanying drawings. These terms, however, are not intended to be overlimiting, except where so specifically noted.

Referring to FIGS. 1-3, there is shown a disposable blood pressure cuff 20 that is made in accordance with a first embodiment. The cuff 20 is defined by a highly flexible sleeve member 30, which according to this exemplary embodiment is made from a thin cellulosic material such as paper. The sleeve member 30 is formed by suitable means and according to this specific version, is constructed from a mailing envelope, though other suitable configurations can easily be imagined. Preferably, a stabilizing mesh made from fiber is preferably incorporated within the flexible sleeve member 30 to aid in wearability. Other suitable materials can be utilized, provided these materials are preferably tear-resistant, including certain so-called "green" or environmentally friendly, including compostable materials or recyclable materials, such as polypropylene, as described in greater detail in a later embodiment. For example and alternatively, the sleeve member can also be made from a material such as polyethylene and treated with an additive that causes the sleeve member to become biodegradable within a predetermined time interval (e.g., 2-3 months). Exemplary additives that are useful for this purpose include Green Solutions PDI BD-0701 or Oxo-Degrader.

The envelope-like structure of the flexible sleeve member 30, according to this exemplary version, is made up of a single sheet of material that is folded along one edge to define a pair of planar sleeve portions 34, 38, each sleeve portion having a length dimension that is significantly larger than a corresponding width dimension. The envelope-like structure is created by sealing the remaining edges 42, FIG. 3, of the sleeve 30 by heat sealing, ultrasonic or RF welding or other suitable means. Alternatively, the cuff 20 can be made from multiple sheets and sealed along all peripheral edges thereof.

A slotted region 52 is formed through each of the sleeve portions 34, 38 on one side of the flexible sleeve 30, while a circular opening 56 is provided through an opposite side thereof through one of the planar sheets 34.

According to this exemplary version, an inflatable bladder 60, shown in FIGS. 1, 2, is placed within the interior 46 of the side of the sleeve 30 having the circular opening 56 prior to sealing of the peripheral edge 42, FIG. 3. Alternatively, an inflatable portion of the flexible sleeve member 30 can be sealed on all edges, including an interior bordering edge 45, FIG. 3, thereof as described in a later embodiment. An exterior port is provided herein in the form of a socket 64 that extends from the bladder 60 and communicates fluidly with the interior thereof. The socket 64 is defined herein as an open-ended cylindrical cavity having a circumferential lip 67, which according to this embodiment extends from the exterior of the bladder 60 and is sized to extend through the circular opening 56 of the sleeve member 30. It will be readily apparent that the opening 56 can assume other shapes depending on the socket or port that is used therewith; for example, a hexagonal or other suitably shaped opening and port could be utilized. An opening 68 within the socket 64 extends into the interior of the bladder 60. As a result, the socket 64 enables fluid as well as mechanical interconnection with blood pressure measuring apparatus including a gage housing or hose adapter by way of a releasable snap-fitting connection. Additional details concerning a suitable socket design are provided in commonly owned and co-pending U.S. Ser. No. 09/669,474, the entire contents of which are herein incorporated by reference.

The bladder 60 according to this embodiment is defined by a fluid-impermeable and flexible material and is further defined by a substantially rectangular configuration. It should be noted, however, that this shape should not be limiting, meaning other suitable geometries can be easily utilized. The bladder 60 can be inflated, as described in greater detail below by pneumatic means, such as a pump or bulb (not shown) attached preferably in releasable fashion to the socket 64.

The slotted portion 52, as noted above, extends through each of the sleeve portions 34, 38 and along the major dimension of the sleeve member 30 opposite that of the bladder 60. The major dimension of the slotted portion 52 is aligned with the port 56 and is configured, as shown in FIG. 4, to provide a means of limiting the degree of wrapping of the cuff 20 about the limb of a patient (not shown) when the sheets are looped. As a result, the range of arm sizes that the cuff can be used is limited. The sleeve 30 can be retained in a wrapped form, such as by means of an adhesive, hook and loop fasteners, clips or other suitable attachment means.

As shown in FIG. 4, the cuff 20 can receive pneumatic means and be wrapped about the limb of a patient (not shown). The sleeve member 30 can be equipped with hooks, clips or other fastening means such as hook and loop fasteners (not shown) provided on opposite sides of the sleeve member 30. In this instance, a connector or adapter 84 is releasably snap-fitted to the socket 64, this connector enabling the sleeve 30 to be attached to a plurality of blood pressure measuring devices by means of lumen connectors 88, this connector being more thoroughly described in commonly assigned U.S. Ser. No. 11/513,608, the entire contents of which are herein incorporated by reference. According to another version, the engagement end of a gage housing (not shown) can be snap-fitted directly to the socket 64, FIG. 1, thereby mechanically and fluidly connecting a movement mechanism contained within the gage housing with the sleeve member 30. The gage housing can support either of a mechanical or electronic blood pressure gauge.

Following use by a patient/caregiver, the cuff 20 can be removed from the patient and discarded. Alternatively, the cuff 20 can be used in connection with a single patient, for example, over the course of a patient visit or a typical hospital stay. In order to indicate to the patient/caregiver that the cuff 20 has already been used, a number of use indicators may be integrated into the cuff such as, for example, a removable tab or sheet (not shown) covering the opening 68 of the socket 64 or within the slotted region 52, requiring removal before use of the cuff 20. The cuff 20 may also include an ink packet (not shown) configured to break and discolor the cuff 20 after use.

Another use indicator may include requiring a user to release a folded portion of the cuff 20 that has been attached to another portion of the cuff by heat sealing, ultrasonic or RF welding or other suitable means. Additionally, and as described below, means can be provided for disabling the cuff 20 from being wrapped either once the cuff is removed or after a predetermined number of patient uses.

Referring to FIGS. 5 and 6, there is shown a disposable blood pressure cuff 100 made in accordance with a second exemplary embodiment. The cuff 100 according to this version is defined by a flexible sleeve member 102 that is made from a durable, flexible and fluid-impermeable material such as polyethylene, polyester, polyvinylchloride, or polypropylene, which in the case of the polyethylene can be treated with an additive that enables the sleeve member to become biodegradable after a predetermined and finite period of time. Exemplary additives that permit biodegradability include PPI Green Solutions Additive, Oxo Degrader, among others. Alternatively and in the case of polyester, polyvinylchloride, or polypropylene, the entire cuff can be made one of such materials, enabling recyclability as described in greater detail in a succeeding embodiment. According to this embodiment, the cuff 100 is formed from a single planar sheet formed into a folded configuration, the peripheral edges 112 of which are welded, bonded or otherwise sealed together in order to define a sleeve-like structure. Additionally, an intermediate transverse edge 112 is also sealed, thereby creating a sealed inflatable compartment 114 in lieu of a bladder. The material used according to this embodiment is fluid-impermeable and sufficiently flexible and resilient to permit expansion/inflation.

A small circular opening is cut into one of the planar sheets 104 of the formed cuff 100 over which is disposed a port or socket 110, the latter of which includes a circumferential or annular lip 117. According to this embodiment, the socket 110 is made from a flexible material such as polypropylene, polyester, polyvinylchloride, or polyethylene. The socket 110 according to this embodiment extends above the exterior surface of the planar sheet 104 and includes an opening 111 which extends into the interior of the inflatable portion 114 enabling fluid interconnection. The socket 110 is attached to a support structure 118 that is bonded or is otherwise sealed, according to this embodiment, to the exterior of the planar sheet 104. Alternatively, the support structure can be welded to the interior of the planar sheet with the socket extending directly through the opening. A plurality of angled protrusions 122 extend in spaced linear relation on opposing sides of the socket 110 on the exterior of the support structure 118. The protrusions 122 are also preferably made from a plastic material, such as polypropylene, polyester, polyvinylchloride, or polyethylene. The inflatable portion 114 of the sleeve member 102 is sealed on all four sides or edges 112, 115 by means of heat sealing, RF or ultrasonic welding or other appropriate techniques that provide a fluid-impermeable seal, wherein the material of at least the inflatable portion of the sleeve is made from a fluid-impermeable material and is flexible to enable expansion for inflation thereof by pneumatic means (not shown).

On the opposite side of the sleeve member 102 from the inflatable portion 114, a slotted portion 126 is provided having a major dimension aligned with the major dimension (length) of the sleeve member. The slotted portion 126 extends through each of the planar sheets 104 and 108 (not shown) defining the sleeve member 102 and is used in conjunction with the socket 114 to control the range of limb sizes to which the cuff 100 can be utilized. A series of small openings 132 are disposed in spaced linear fashion along each lateral side of the slotted portion 126 and substantially along the length thereof, the openings each being sized to retain a raised protrusion 122 and the slotted portion 126 being sized to retain the socket 110.

Figure 7:
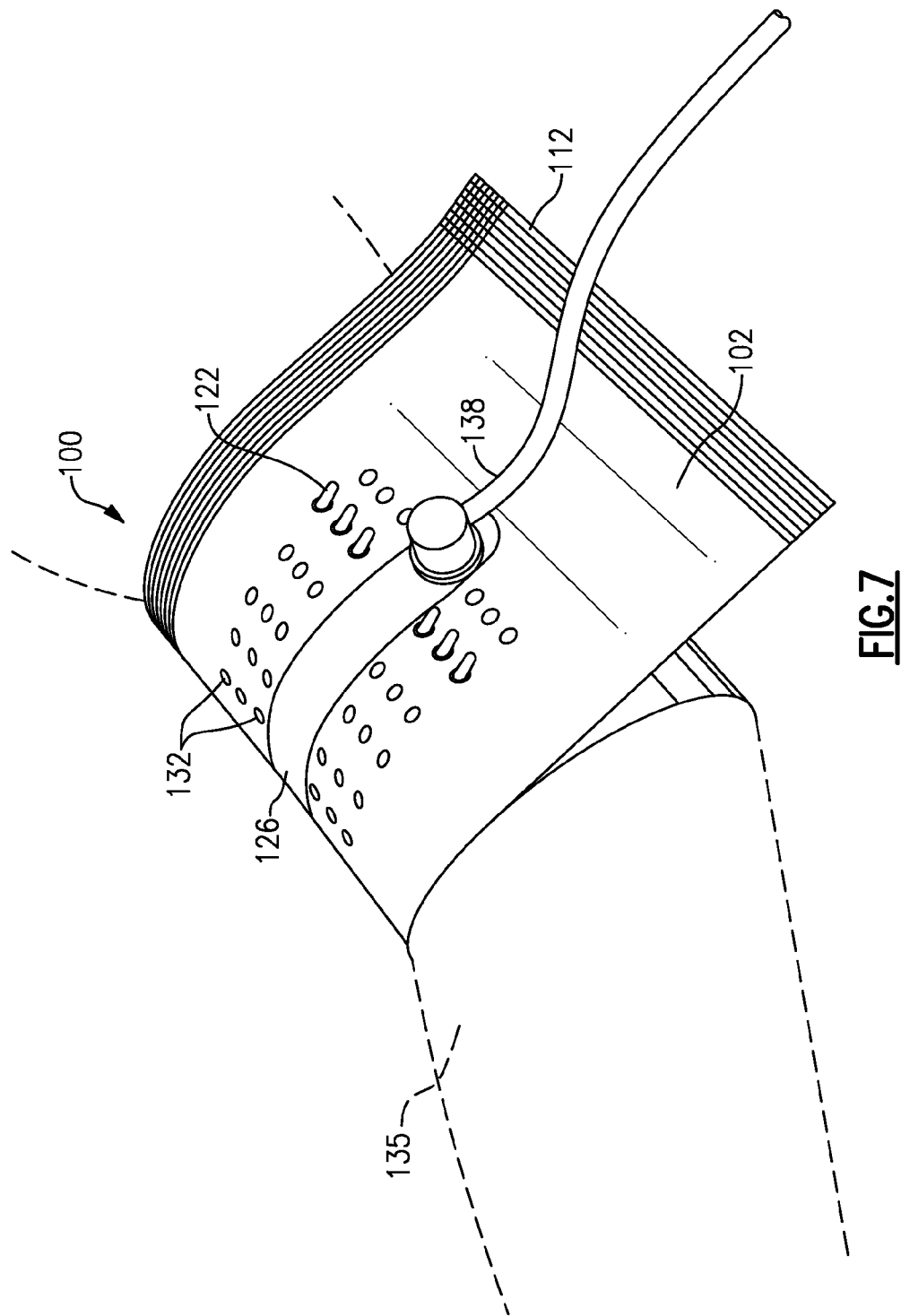
FIG. 7 illustrates the disposable blood pressure cuff of FIGS. 5 and 6, as wrapped about a limb of a patient.

In use and referring to FIG. 7, the sleeve member 102 is wrapped about the limb (arm) 135 of a patient wherein the socket 110 extends through the slotted portion 126 and the angled raised protrusions 122 are aligned with and fitted to a row of the spaced openings 132. The slotted portion 126 is sized to only permit attachment to a range of patient limb sizes (circumferences). Pneumatic means 138 (shown partially) extending to a measuring apparatus (not shown) can be attached in releasable fashion to the socket 110 and the inflatable portion 114, FIG. 6, of the flexible sleeve member 102 can be inflated for measurement. Following use, the pneumatic means 138 are removed from the extending socket 110 and the protrusions 122 are removed from the openings 132. In one version, removal of the protrusions 122 from the openings 132 can cause the openings to tear and therefore disable re-use of the cuff.

Referring to FIGS. 8-11, there is disclosed an ecologically friendly blood pressure cuff 150 that is made in accordance with another exemplary embodiment. The cuff 150 according to this embodiment is made from at least one or a pair of planar sheets made from a biodegradable and highly flexible material, each sheet having a first side that is fluid impermeable and the remaining side being non-woven. According to the present embodiment, a pair of sheets 154 consisting of a fluid impermeable side made from polypropylene and a non-woven side made from polyethylene that are sealed together to form a single sheet. One or two sheets 154 are used wherein the fluid impermeable sides (not shown) of each sheet are placed into adjacent relation to create a cuff interior and the nonwoven sides form an exterior in which all of the peripheral edges 156 are sealed by appropriate means, such as heat sealing, ultrasonic or RF welding.

Alternatively, the entire cuff can be made from a single material, such as polypropylene, enabling recyclability. Referring to the embodiment in FIGS. 8b and 8c, sheet 154, which includes slotted portion 170, preferably comprises a film on the surface of sheet 154 including the hook fastener portion 162 and a non-woven fabric laminated to the film forming a top surface of the sheet 154. The film in this embodiment has a thickness of about 0.002 to 0.008 inches, and preferably 0.0025 to 0.0055 inches, and a weight of about 1.0 to 7.0 ounces per square yard, and preferably 1.2 to 4.6 ounces per square yard. Additionally, the non-woven fabric of this embodiment has a weight of about 0.5 to 3.0 ounces per square yard, and preferably 0.9 to 1.4 ounces per square yard. The resulting laminated fabric of this embodiment will have a resulting weight of about 1.5 to 15.0 ounces per square yard, and preferably about 2.1 to 6.0 ounces per square yard. A creep elongation of the laminated fabric, as measured with a one inch by one inch test sample loaded with five pounds over six minutes, should be less than about 0.0065 inches, and preferably less than about 0.0022 inches.

Figure 8A:
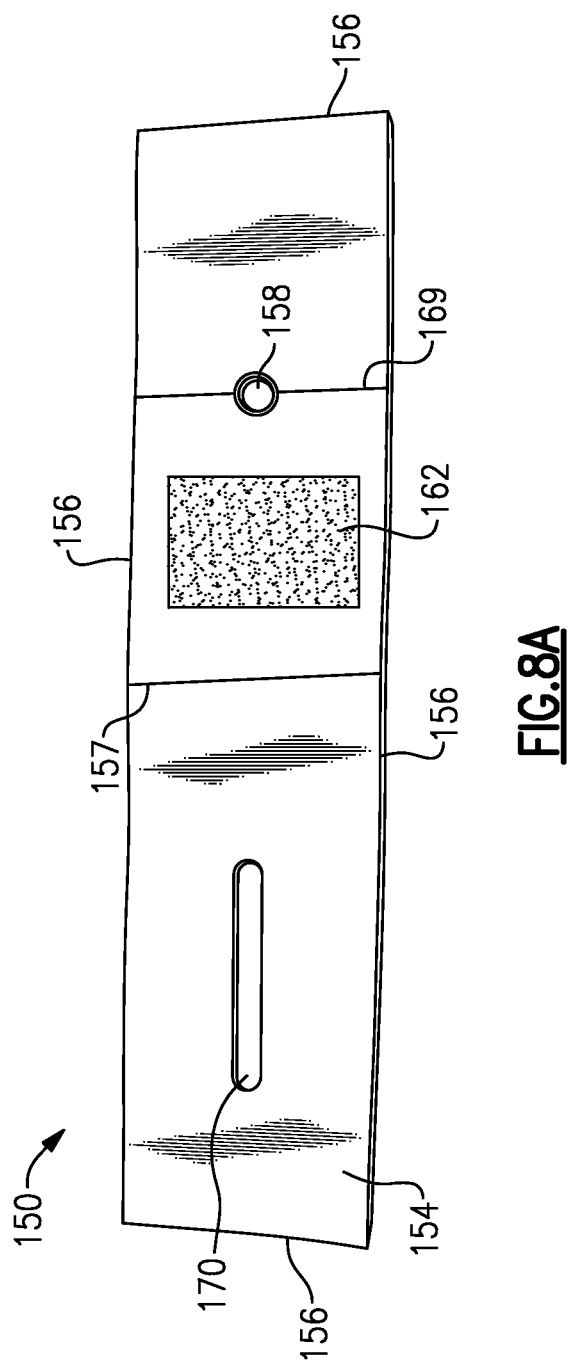
FIG. 8a is a perspective view of a disposable blood pressure cuff made in accordance with another embodiment.

In the embodiment of FIG. 8a, an intermediate transverse seal 157 is also formed at or near the middle of the length dimension of the cuff 150, thereby dividing the cuff into two adjacent sections, one of which is capable of inflation as described herein. An opening is formed in one of the planar sheets 154 in one of the sections wherein a port supported upon a smaller sheet section (not shown), preferably made from the same material as the sheets 154 is bonded to the interior of the sheet, and in which the port herein is defined by a socket 158 that extends through the opening wherein a fluid tight seal is created about the periphery of the socket within the opening. The socket 158 includes a relatively flexible circumferential or annular lip and is also preferably formed from the same material (i.e., polypropylene) as those constituting the sleeve sheets 154. A slotted portion 170 is formed in the opposite side of the cuff 150 wherein the major dimension of the slotted portion is aligned with the extending socket 158. According to this embodiment, the slotted portion 170 and opening/socket are provided at substantially the center of the width dimension of the cuff 150, as shown most clearly in FIG. 8a.

Adjacent the opening and extending socket 158, a hook fastener portion 162 is provided on the exterior of the cuff 150 on one side thereof. In this embodiment, the material of the cuff on the non-woven exterior of the sheets 154 is defined by a micro-structure that creates adhesion with the hook fastener portion 162 when the cuff 150 is wrapped, as shown, for example, according to FIG. 9. Due to the nature of this material, there is no need to provide a separate loop fastener portion to act as closure means for the cuff 150, when secured to the limb of a patient as shown, for example, in FIGS. 10 and 11.

Figure 10:
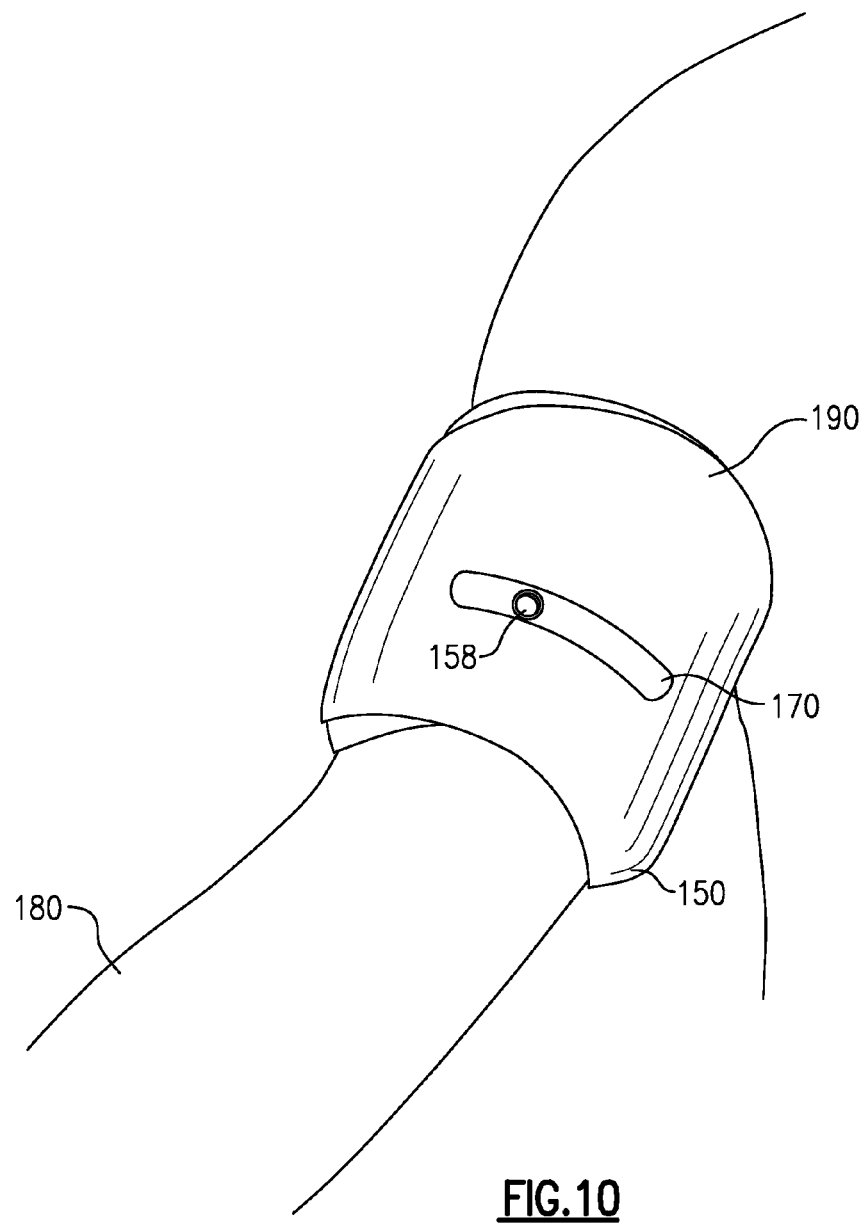
FIGS. 10 and 11 illustrate views of the disposable blood pressure cuff of FIGS. 8 and 9 as wrapped about the limb of a patient, demonstrating that the cuff can be wrapped for use in more than one orientation.

When wrapped, the slotted portion 170 is sized to accommodate the socket 158 and the slotted portion is further sized to be wrapped only within a predetermined range of limb (arm) circumferences. The slotted portion 170 in combination with the extending socket 158 serves numerous functions. First, and as noted the slotted portion 170 will only accommodate a predetermined range of arm circumferences, in which the slotted portion can be formed to accommodate a class of patient (e.g., a child, an adult, a large adult, etc). In addition, the slotted portion 170 serves as a guide to wrapping the cuff 150 about the limb 180, FIG. 10, given that the socket 158 must be fitted within the slotted portion when wrapped. Still further, the use of a slotted portion 170 and socket 158 permits the port to be flexibly located on the cuff 150 without interfering with the attachment, such as those involving hook and loop fasteners. In fact, the hook fastener portion 162 can also be positioned more conveniently along the exterior of the cuff 150 than in previously known cuffs. In this embodiment, the hook fastener portion 162 can be positioned more inboard (that is, inboard relative to the nearest lateral edge 156 of the cuff) such that attachment can occur within the overlapping portion of the cuff 150 that includes the slotted portion 170. By moving the attachment (fastener) portions more inboard, greater adhesion is achieved using less total surface area. Moreover and by selection of materials as in this embodiment, manufacture is simplified in that a separate loop fastener portion is not required given the inherent adhesive quality of the exterior sleeve material.

In this version, the durability of the material is affected with each attachment and subsequent removal of the cuff 150 from the hook fastener portion 162. This degradation of material influences the ability of the material to further adhere in those areas, thereby rendering the cuff 150 incapable of attachment after a finite number of uses. Depending on the material, this finite number of uses could be made to be one or several.

Figure 8B:
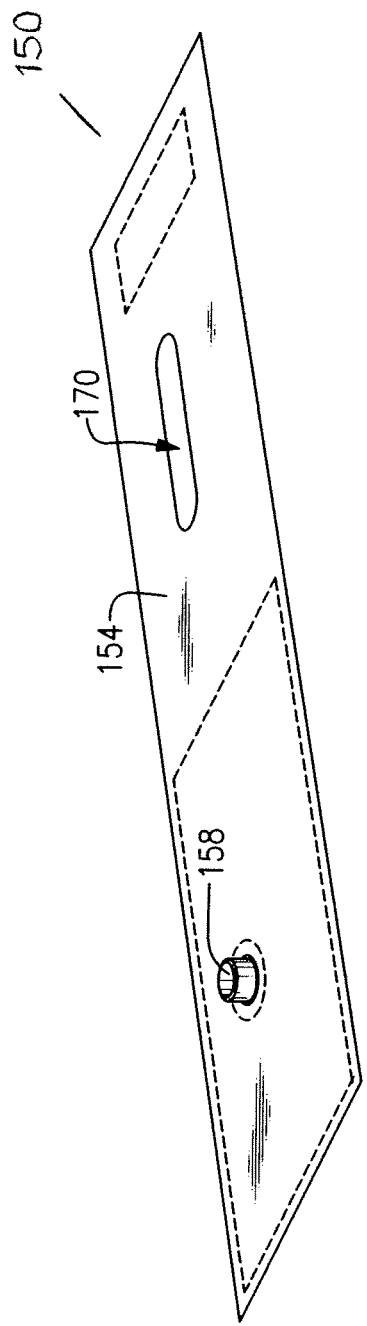
FIG. 8b is a perspective view of a disposable blood pressure cuff made in accordance with yet another embodiment.
Figure 8C:
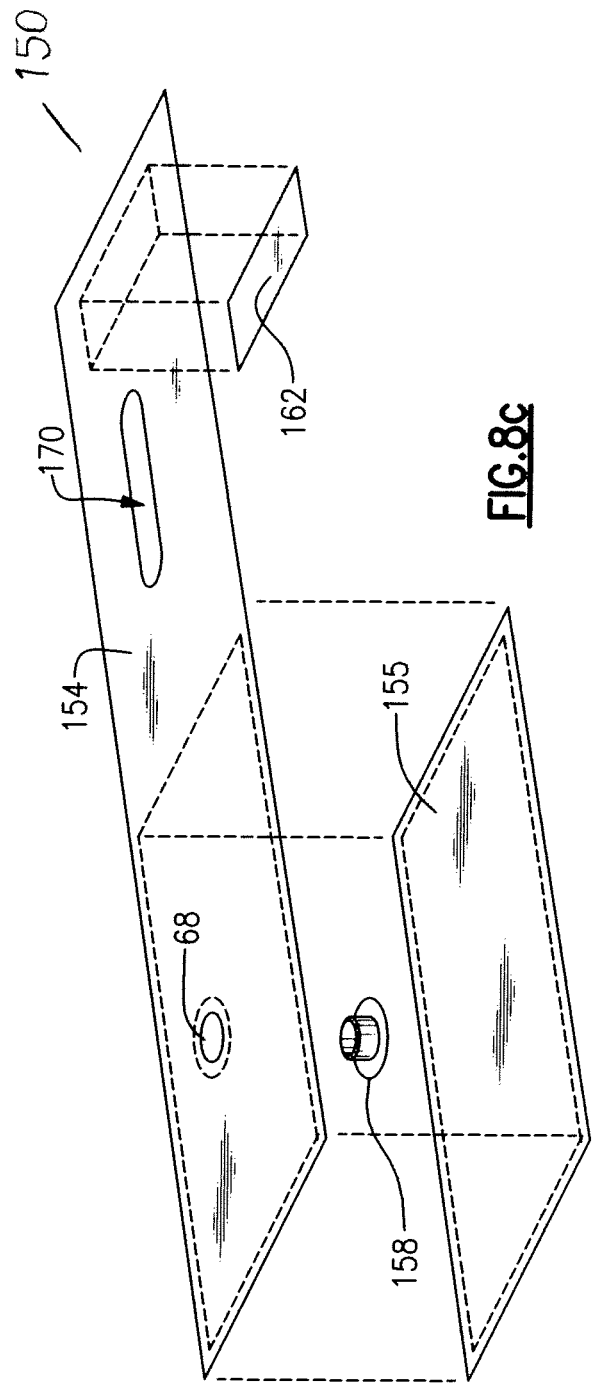
FIG. 8c is an exploded view of the disposable blood pressure cuff of FIG. 8b.

FIGS. 8b and 8c illustrate another embodiment of the cuff 150 having a bladder sheet 155 with a length shorter than the length of both the sheet 154 and the cuff 150. The cuff 150 according to this embodiment is made from sealing the bladder sheet 155 to the sheet 154 in at least a region around the opening 68 to form a single sheet. In this configuration, an interior-inflatable portion is created between sheet 154 and bladder sheet 155 with the opening 68 fluidly interconnecting the interior-inflatable portion with the exterior of the cuff 150. A socket 158, as described above, extends through the opening 68 wherein a fluid tight seal is created about the periphery of the socket within the opening. The slotted portion 170 and opening/socket 68/158 are provided at substantially the center of the width dimension of the cuff 150, while the hook fastener portion 162 is also provided on sheet 154 on the side including bladder sheet 155.

In the embodiment in FIGS. 8d and 8e of the cuff 150, sheet 154 comprises a substantially L-shaped configuration generally having a lateral area, a central area, and a vertical area. The lateral area includes slotted portion 170, and hook fastener portion 162, while the central area includes the opening 68. The cuff 150 is formed with this embodiment by folding the vertical area under the central area along folded portion 159 of the sheet 154. A socket 158 is also extended through opening 68 and attached to sheet 154 as described above. A bladder is then formed by sealing all peripheral edges between the central and vertical areas, except for areas around folded portion 159, which already form a fluid impermeable barrier. The slotted portion 170 and opening/socket 68/158 are provided at substantially the center of the width dimension of the cuff 150, while hook fastener portion 162 is also provided on sheet 154 on the surface where the vertical area is attached to the central area of the sheet 154.

Figure 8F:
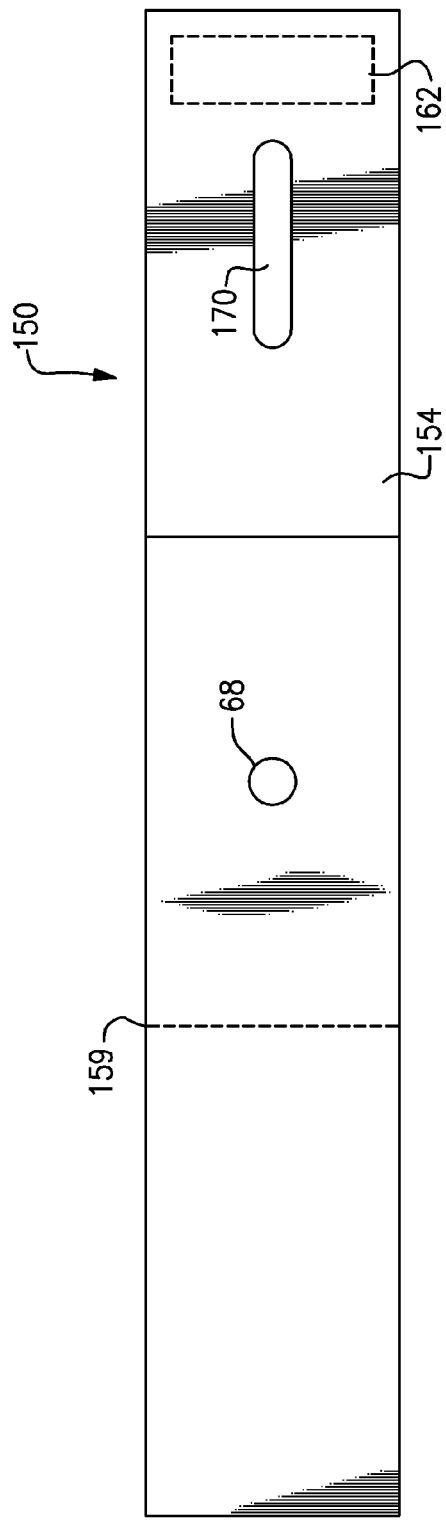
FIG. 8f is a perspective view of an unfolded disposable blood pressure cuff made in accordance with yet another embodiment.
Figure 8G:
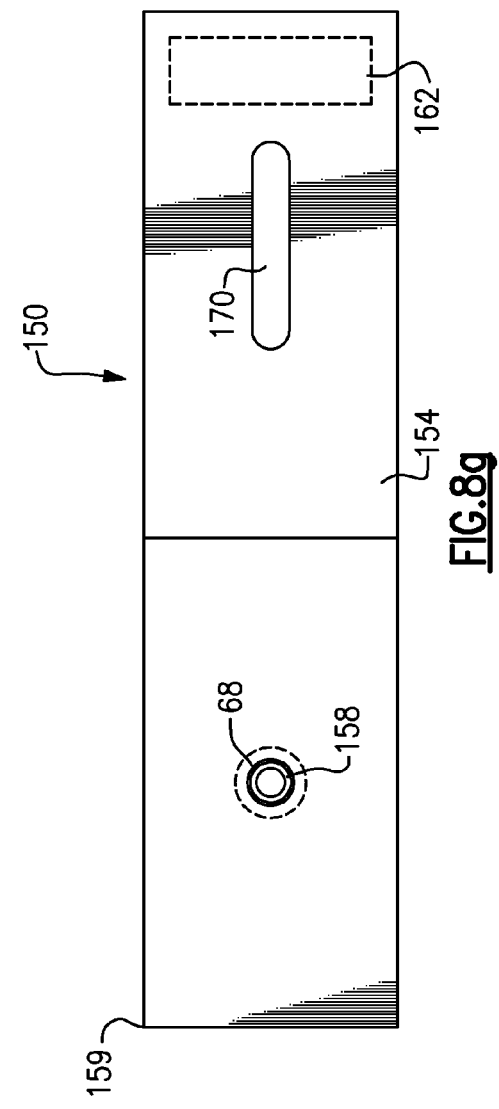
FIG. 8g is a perspective view of the disposable blood pressure cuff of FIG. 8f in an assembled state.

FIGS. 8f and 8g illustrate an additional embodiment of the cuff 150, in which sheet 154 comprises a substantially rectangular configuration generally having a left-lateral area, a central area, and a right-lateral area. The right-lateral area includes slotted portion 170, and hook fastener portion 162, while the central area includes the opening 68. Forming the cuff of this embodiment includes folding the left-lateral area under the central area along folded portion 159 of the sheet 154. A socket 158 is also extended through opening 68 and attached to sheet 154 as described above. Sealing all peripheral edges between the central and left-lateral areas, except for areas around folded portion 159, acts to form a bladder. The slotted portion 170 and opening/socket 68/158 are provided at substantially the center of the width dimension of the cuff 150, while hook fastener portion 162 is also provided on sheet 154 on the surface where the left-lateral area is attached to the central area of the sheet 154.

Optionally, a stethoscope pocket (not shown) is formed on the cuff of FIGS. 8a-8g by attaching a pocket sheet (not shown) to the bladder sheet 155 on the surface of the bladder sheet 155 that is exposed when the cuff 150 is assembled. More specifically, the pocket is formed with a planar sheet consisting of material the same or similar to sheet 154 or bladder sheet 155. The sheet forming the pocket has a substantially rectangular configuration. It should be noted, however, that this shape should not be limiting, meaning other suitable geometries can be easily utilized. The length dimension of the pocket sheet approximates the width of the bladder sheet 155 and has a width smaller than its length and approximating the diameter of a typical stethoscope head. The pocket sheet is positioned on the exposed surface of the bladder sheet 155 by aligning each width edge of the pocket sheet near and parallel to a length edge of the bladder sheet. The pocket structure is then created by attaching both length edges of the pocket sheet by heat sealing, ultrasonic or RF welding, or other suitable means.

Figure 11:
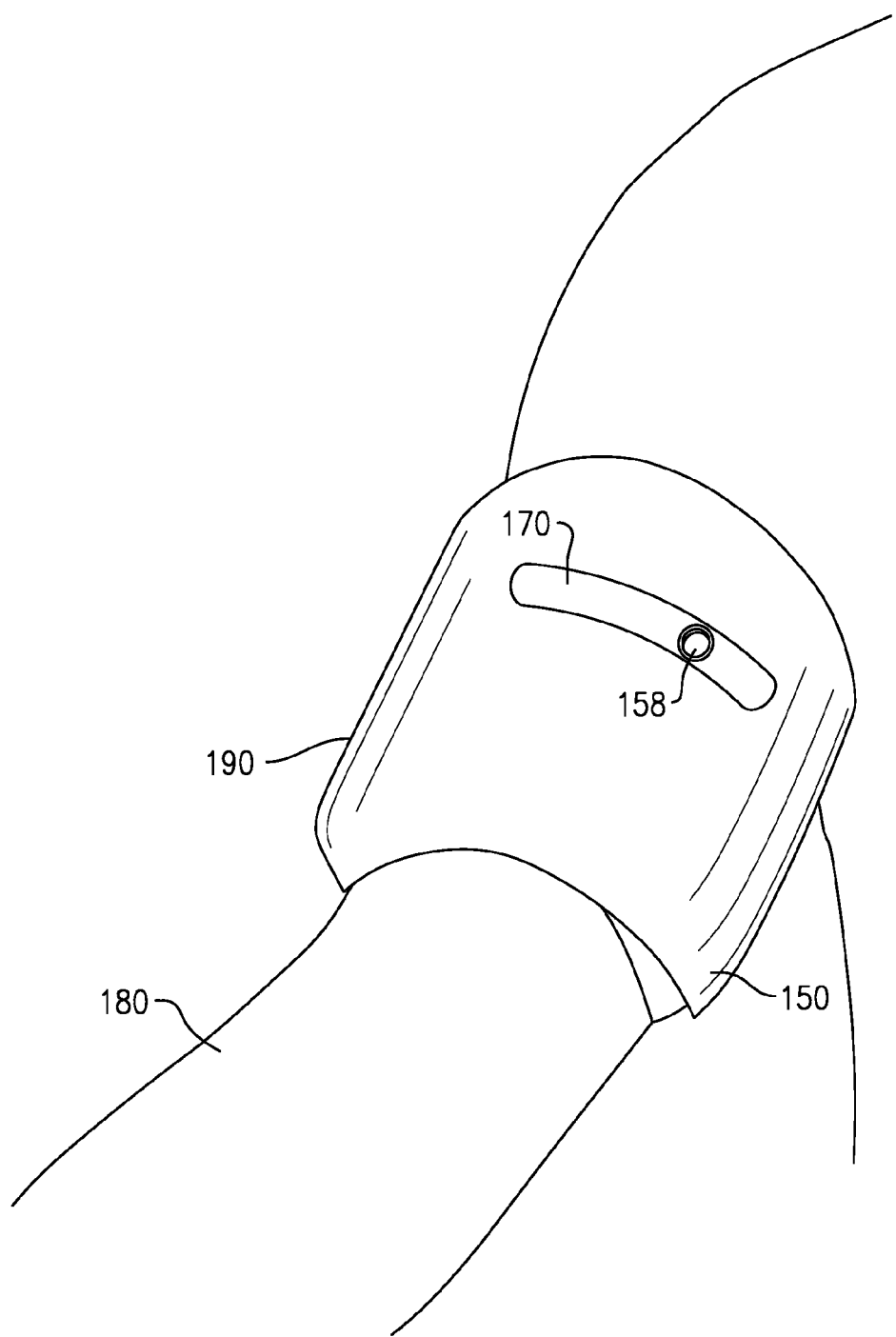

Referring to FIGS. 10 and 11, the cuff 150 is shown in a wrapped condition about a limb 180 of a patient. For purposes of clarity, only the cuff 150 is shown and not the remainder of associated blood pressure apparatus. As seen from these views, the cuff can be wrapped in at least two separate wrapped orientations, see the relative position of a marker 190 denoted to indicate positional differences on the cuff 150 for clarity purposes. A marker 190 can also be added to the cuff 150 to identify a patient or customize the cuff 150.

Either wrapped orientation is made possible due to the "on-center" positioning of the port/socket 158 and the slotted portion 170 since the port is positioned in the same location on the limb 180 of the patient in either instance. As such, neither orientation negatively affects the operation of the cuff 150 in obtaining a blood pressure measurement from the patient. In addition, the port itself due to the symmetrical positioning thereof on the sleeve can also be used as an arterial marker, eliminating the need to add a specific marker to the cuff 150.

By making the entire cuff as described herein from the same material, in this case polypropylene, the cuff can easily be recycled following use. Optionally, the cuff 150 can be classified as a category 5 recyclable product when the entire cuff 150, including the socket 158, is manufactured from approved types of polypropylene. In the cases where the cuff 150 is made entirely from polyethylene, the cuff can be classified as a #2 or #4 recyclable product, or as a #1 recyclable product where the cuff is made from polyester. Moreover and even in the instance in which the cuff is not made entirely from a homogenous material, the herein described sleeve when incinerated does not release toxic and ozone depleting gases as in the case of those sleeves containing polyvinylchloride (PVC). For those cuffs to which are treated with additives including those previously noted above, the cuffs are rendered biodegradable after a predetermined time period. In effect, the herein described cuffs are designed to be ecologically and environmentally friendly, whether through recyclability or biodegradability.

Referring to FIG. 12, the flexible nature of the herein described recyclable or biodegradable blood pressure cuffs enables additional versatility in the packaging and dispensing of same. By way of example, a cuff dispense container 200 can include a plurality of disposable, single patient or single patient-use cuffs, such as those made in accordance with FIG. 8 that are arranged in a stacked configuration. In one version, the cuffs 20 can be folded in half and nested one within the next succeeding cuff with the sockets facing the dispense slot of the container 200. It should be noted that other stacking configurations can easily be imagined, such as a roll, given the highly flexible nature of the herein described cuffs 150. The dispense container 200 according to this version is a cardboard or paper dispenser, which retains the contained stacked configuration of cuffs 150 (only one of which is shown), the container having a dispense slot 204 in a top or upper surface 208 of the container that is sized to dispense the cuffs individually (i.e. one at a time) to a user by pulling a portion of a cuff 150 extending therethrough in which the action of pulling a cuff for dispense pulls another succeeding cuff in the stacked configuration toward the slot 204. Though the dispenser 200 is shown herein for pulling cuffs 150 upwardly, it will be readily apparent that the dispenser can assume other attitudes and orientations (i.e., top slot facing downward, side or lateral dispense, etc.).

A plurality of cuffs, such as described above, can be otherwise stored for dispensing. For example, the herein described ecologically friendly cuffs can be disposed individually in a roll form such as described in U.S. Pat. No. 5,819,739, the entire contents of which are herein incorporated by reference. Still other dispensing techniques can easily be imagined.

PARTS LIST FOR FIGS. 1-12

20 cuff, recyclable or biodegradable
30 sleeve member, flexible
34 planar sheet
38 planar sheet
42 peripheral edges
45 seal, intermediate
46 interior
52 slotted region
56 opening
60 bladder
64 socket
67 circumferential lip
68 opening
84 hose adapter
88 ports
100 cuff, recyclable
102 flexible sleeve member
104 planar sheet
108 planar sheet
110 socket
111 opening
112 peripheral edge seals
114 inflatable portion
115 intermediate seal
117 circumferential lip
118 structure, support
122 angled protrusions
126 slotted portion
132 openings, spaced
135 limb, patient
150 recyclable blood pressure cuff
154 sheets, planar
155 bladder sheet
156 peripheral edge
157 transverse seal, edge
158 socket
159 fold portion
162 hook fastener portion
169 artery marker
170 slotted portion
180 limb
190 marker, cuff
200 container, dispensing
204 slot, dispense
208 top surface It will be readily apparent that other modifications and variations can be made in accordance with the inventive aspects that are described herein and that the embodiments described are not intended to be exhaustive. For example, an ecologically friendly cuff can also be made using a combination of polyethylene and polypropylene including a polyethylene interior and the non-woven polypropylene exterior previously described with regard to cuff 150. Other suitable versions within the teachings provided herein should easily be contemplated as now further defined according to the following claims.

The invention claimed is:

1. A blood pressure cuff, the cuff comprising:
a first sheet having an opening;
a second sheet, wherein the second sheet is attached to a bottom of the first sheet;
an interior-inflatable portion formed between the bottom of the first sheet and a top of the second sheet, wherein the opening of the first sheet fluidly interconnects the interior-inflatable portion with an exterior of the cuff, the first and second sheets being made from a fluid impermeable material;
a socket attached to said cuff through said opening and having a circumferential lip that directly and releasably engages one of a hose adapter and a gage housing, said socket fluidly interconnecting the exterior of said cuff with said interior-inflatable portion;
a slotted portion formed in a longitudinally extending section of said first sheet spaced apart from the interior-inflatable portion; and
fastener material disposed on the cuff proximate an end of the longitudinally extending section wherein the cuff is configured to wrap around a limb of a patient during blood pressure measurement such that the fastener material adheres to a top surface of the first sheet and the slotted portion receives the socket and wherein the length of slotted portion and positioning of the socket on the cuff are selected to limit the circumference of the cuff in the configuration during blood pressure measurement when the socket is received in the portion.

2. A cuff as recited in claim 1, wherein the cuff further comprises means for indicating that the cuff has already been used.

3. A cuff as recited in claim 2, wherein means for indicating that the cuff has already been used includes alteration of a color of a treated portion of the cuff after exposure to light.

4. A cuff as recited in claim 1, wherein the fastener material is a hook, made from the fluid impermeable material, attached to a bottom of the first sheet and spaced apart from the second sheet.

5. A cuff as recited in claim 4, wherein the hook is attached to an end portion of the first sheet and on a side of the first sheet including the slotted portion.

6. A cuff as recited in claim 4, wherein a top of the first sheet further comprises a loop fastener configured to engage the hook.

7. A cuff as recited in claim 6, wherein the top of the first sheet comprises a non-woven fibrous material.

8. A cuff as recited in claim 6, wherein the non-woven fibrous material has a weight of about 0.5 to 3.0 ounces per square yard.

9. A cuff as recited in claim 6, wherein a film is laminated to the bottom of the first sheet.

10. A cuff as recited in claim 9, wherein the film has a thickness of about 0.002 to 0.008 inches and a weight of about 1.0 to 7.0 ounces per square yard.

11. A cuff as recited in claim 9, wherein the first sheet has a creep elongation of less than about 0.0065 inches.

12. A cuff as recited in claim 6, wherein the bottom of the first sheet has a smooth texture.

13. A cuff as recited in claim 6, wherein the loop fasteners are degraded upon attachment and subsequent removal from the hook.

14. A cuff as recited in claim 1, wherein the top of the second sheet comprises a non-woven fibrous material configured to resist engagement of the fastener material.

15. A cuff as recited in claim 1, wherein the fluid impermeable material is a recyclable material selected from the group consisting of polypropylene, polyester, polyvinylchloride, and polyethylene.

16. A cuff as recited in claim 1, wherein a length of the first sheet is sized to allow the cuff to be wrapped around a limb at least two times.

17. A cuff as recited in claim 1, wherein the fastener material engages with a portion of the first sheet apart from the inflatable portion of the first sheet.

18. A cuff as recited in claim 1, wherein the cuff is entirely made from the same material.

19. A cuff as recited in claim 1, wherein the longitudinally extending portion is sized to fully overlap the inflatable portion when wrapped.

20. A blood pressure cuff comprising:
- a first sheet and a second sheet, each of said first and second sheets having a first side and a second side;
- an inflatable compartment defined over a portion of said cuff, said inflatable chamber being defined between the second side of said first sheet and the first side of said second sheet, said inflatable compartment being sized to be wrapped circumferentially about the limb of a patient;
- a cylindrical portion extending outwardly from said cuff having an opening that fluidly interconnects with the interior of said inflatable compartment;
- wherein at least one of said first and second sheets extends axially from said inflatable compartment defining a longitudinally extending section;
- fastener material disposed on the cuff proximate an end of the longitudinally extending section and
- a slotted portion formed in said at least one extending section and spaced apart from the inflatable compartment, wherein the cuff is configured to wrap around a limb of a patient during blood pressure measurement such that the fastener material adheres to a top surface of one of the first and second sheets and the slotted portion receives the cylindrical portion and wherein the length of the slotted portion and positioning of the cylindrical portion on the cuff are selected to limit the circumference of the cuff in the configuration during blood pressure measurement when the cylindrical portion is received in the slotted portion.

21. A cuff as recited in claim 20, wherein said slotted portion and said cylindrical portion are centrally aligned relative to a width dimension of said cuff.

22. A cuff as recited in claim 20, wherein said longitudinally extending section includes a hook fastener portion at an extending end thereof and in which said the opposite side of said first sheet includes the fastener material that enables adhesion to said hook fastener portion.

23. A cuff as recited in claim 22, wherein said material of said first sheet is configured to degrade based on detachment of said hook fastener portion from the fastener material, such that said cuff is incapable of being secured after a finite number of uses.

24. A cuff as recited in claim 20, wherein the first sheet comprises a non-woven fibrous material.

25. A cuff as recited in claim 20, wherein said first sheet has a creep elongation of less than about 0.0065 inches.

26. A cuff as recited in claim 20, wherein the entire cuff is commonly made from the same material.

27. A cuff as recited in claim 20, wherein the longitudinally extending portion is sized to fully overlap the inflatable compartment when wrapped.

* * * * *

UNITED STATES PATENT AND TRADEMARK OFFICE
CERTIFICATE OF CORRECTION

PATENT NO.         : 8,652,057 B2
APPLICATION NO.    : 12/704638
DATED              : February 18, 2014
INVENTOR(S)        : Robert L. Vivenzio et al.

Page 1 of 1

It is certified that error appears in the above-identified patent and that said Letters Patent is hereby corrected as shown below:

In the Claims:

Col. 13, line 32, per Amendment filed on August 5, 2013 for claim 35 (final claim 20): remove the word "axially". Column 13, lines 31-33 should read as follows:

-- wherein at least one of said first and second sheets extends from said inflatable compartment defining a longitudinally extending section; --

Signed and Sealed this
Twenty-seventh Day of May, 2014

Michelle K. Lee
*Deputy Director of the United States Patent and Trademark Office*